United States Patent [19]

Khanna et al.

[11] Patent Number: 4,990,518

[45] Date of Patent: Feb. 5, 1991

[54] PHARMACOLOGICALLY ACTIVE HETEROARYL SUBSTITUTED IMIDAZO (4,5-c) PYRIDINES

[75] Inventors: Ish K. Khanna, Vernon Hills; Richard M. Weier, Lake Bluff, both of Ill.

[73] Assignee: G. D. Searle & Co., Chicago, Ill.

[21] Appl. No.: 406,674

[22] Filed: Sep. 13, 1989

[51] Int. Cl.$^5$ .................. A61K 31/44; C07D 471/04
[52] U.S. Cl. .................................. 514/303; 546/118
[58] Field of Search ..................... 546/118; 514/303

[56] References Cited

U.S. PATENT DOCUMENTS

| | | | |
|---|---|---|---|
| 4,327,100 | 4/1982 | Austel et al. | 546/118 |
| 4,336,257 | 6/1982 | Baldwin | 546/118 |
| 4,716,160 | 12/1981 | Markwell et al. | 546/119 |
| 4,804,658 | 2/1989 | Manley | 514/303 |
| 4,914,108 | 4/1990 | Khanna et al. | 546/118 |

OTHER PUBLICATIONS

EP Application 87 113 294.0, Published Mar. 23, 1988.
EP Application 87 114 979.5, Published Apr. 20, 1988.
EP Application 87 114 841.7, Published May 18, 1988.
EP Application 83302433.4, Published Nov. 9, 1983.

*Primary Examiner*—Mary C. Lee
*Assistant Examiner*—Bernard I. Dentz
*Attorney, Agent, or Firm*—Joy Ann Serauskas; Paul D. Matukaitis

[57] ABSTRACT

This invention relates to substituted imidazopyridine derivatives having the follow formula

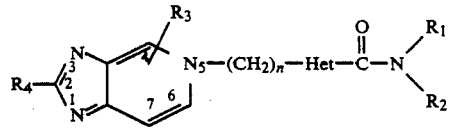

or a pharmaceutically acceptable acid addition salt thereof: wherein the variables are described in the specification are useful in the treatment of diseases or disorders mediated by platelet-activating factor. This invention also relates to pharmaceutical compositions of such substituted imidazopyridines.

14 Claims, No Drawings

PHARMACOLOGICALLY ACTIVE HETEROARYL SUBSTITUTED IMIDAZO (4,5-C) PYRIDINES

FIELD OF THE INVENTION

This invention is in the field of mammalian therapeutics and relates to compounds for treatment of mammalian diseases such as inflammation, cardiovascular disorders, asthma and other diseases. Of particular interest is a class of Heteroaryl Substituted Imidazo [4,5-c]Pyridines useful for treatment of cardiovascular and immuno-inflammatory related disorders mediated by platelet activating factor (PAF).

BACKGROUND OF THE INVENTION

Platelet-activating factor (PAF) has been associated with various biological activities and pathways, thus making it an important mediator responsible for a variety of physioloqical processes including, but not limited to, activation and aggregation of platelets, smooth muscle contraction, pathogenesis of immune complex deposition, inflammation, and respiratory, cardiovascular and intravascular alterations. These physiological processes are associated with a large group of diseases, such as, for example, cardiovascular disorders, asthma, lung edema, endotoxin shock, adult respiratory distress syndrome and inflammatory diseases.

U.S. Pat. No. 4,804,658 discloses a class of imidazopyridine derivatives useful in the treatment of diseases or disorders mediated by platelet-activating factor. The present invention is distinct from this disclosure in that in the present invention a heteroaryl carboxamide is attached to the nitrogen (position 5) which makes up the six membered ring of the imidazopyridine ring system as opposed to the disclosure wherein a benzamide moiety is attached to one of the nitrogens which makes up the five membered ring of the imidazopyridine ring system.

SUMMARY OF THE INVENTION

The present invention relates to a novel class of compounds represented by the formula

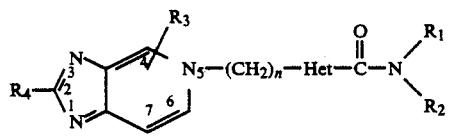

or a pharmaceutically acceptable acid addition salt thereof: wherein

R<sub>1</sub> and R<sub>2</sub> are each independently selected from hydrogen; straight or branched chain alkyl of 1 to 15 carbon atoms; cycloalkyl of 3 to 8 carbon atoms; substituted cycloalkyl which can be substituted once or more by alkyl of 1 to 6 carbon atoms; phenyl; phenyl which can be substituted once or more by alkyl of 1 to 6 carbon atoms or halogen; straiqht or branched alkenyl having 3 to 15 carbon atoms with the proviso that the double bond of the alkenyl group cannot be adjacent to the nitrogen.

Het is a heteroaromatic ring having 5 atoms wherein said atoms are selected from carbon, nitrogen, oxygen or sulfur and wherein any of the carbon atoms can be optionally substituted with a substituent independently selected from the group consisting of alkyl of 1 to 6 carbon atoms, alkoxy wherein the alkyl is 1 to 6 carbon atoms and halogen selected from bromo, fluoro, or chloro with the proviso that the carboxamide and imidazopyridine groups cannot be ortho to each other and a nitrogen hetero atom of the heteroaryl ring is substituted by hydrogen or alkyl of 1 to 6 carbon atoms or a heteroaromatic ring having 6 atoms wherein said atoms are selected from carbon and nitrogen and wherein any of the carbon atoms can be optionally substituted with a substituent independently selected from the group consisting of alkyl of 1 to 6 carbon atoms, alkoxy wherein the alkyl is 1 to 6 carbon atoms and halogen selected from bromo, fluoro or chloro with the proviso that the carboxamide and imidazopyridine groups cannot be ortho to each other.

n is an integer from 1 to 5.

R<sub>3</sub> is a group substituted at one or more of the 4, 6 or 7 positions of the pyridine ring said groups being independently selected from hydrogen, alkyl of 1 to 6 carbon atoms; halogen wherein the halogen is selected from bromo, fluoro, or chloro; or alkoxy wherein the alkyl is 1 to 6 carbon atoms.

R<sub>4</sub> is hydrogen or alkyl of 1 to 4 carbon atoms.

The invention further relates to pharmaceutical compositions comprising a compound of formula I. Such compounds and compositions have potent and specific PAF antagonistic activities and are thereby useful in the treatment of various diseases or disorders mediated by the PAF, for example inflammation, cardiovascular disorders, osthma, lung edema, and adult respiratory distress syndrome.

A preferred embodiment of the present invention are compounds of the formula

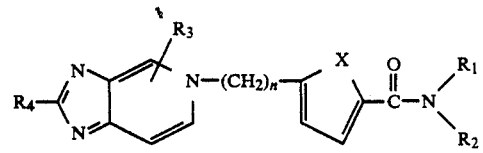

or a pharmaceutically acceptable acid addition salt thereof; wherein

R<sub>1</sub> and R<sub>2</sub> are each independently selected from hydrogen; straight or branched chain alkyl of 1 to 15 carbon atoms; cycloalkyl of 3 to 8 carbon atoms; cycloalkyl which can be substituted one or more by alkyl of 1 to 6 carbon atoms.

R<sub>3</sub> is hydrogen or alkyl of 1 to 6 carbon atoms

R<sub>4</sub> is hydrogen or alkyl of 1 to 4 carbon atoms n is an integer from 1 to 5 x is independently selected from the group consisting of O; S; N-R<sub>5</sub> wherein R<sub>5</sub> can be hydrogen or alkyl or 1 to 6 carbon atoms; or CH=N.

A further embodiment of the present invention are compounds of the formula

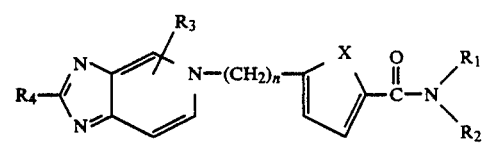

or a pharmaceutically acceptable acid addition salt thereof: wherein

R<sub>1</sub> and R<sub>2</sub> are each independently selected from hydrogen; straight or branched chain alkyl of 1 to 15 carbon atoms; cycloalkyl of 3 to 8 carbon atoms; substituted cycloalkyl which can be substituted one or more by alkyl of 1 to 6 carbon atoms.

$R_3$ is hydrogen or alkyl of 1 to 6 carbon atoms
$R_4$ is hydrogen or alkyl of 1 to 4 carbon atoms
n is an integer from 1 to 5
x is oxygen or CH=N As used herein the term "alkyl of 1 to 15 carbon atoms": refers to straight chain or branched chain hydrocarbon groups having from one to fifteen carbon atoms. Illustrative of such alkyl groups are methyl, ethyl, propyl isopropyl, butyl, isobutyl, pentyl, neopentyl, hexyl, isohexyl, octyl, decyl and the like.

As used herein the term "cycloalkyl of 3 to 8 carbon atoms" included cycloalkyl groups having from three to eight carbons. Illustrative of such cycloalkyl groups are cyclopropyl, cyclobutyl, cyclopentyl, cyclohexyl, cycloheptyl, cyclooctyl and the like.

As used herein the term halogen includes fluoro, chloro and bromo.

As used herein the term "alkenyl having 2 to 15 carbon atoms" refers to straight or branched unsaturated hydrocarbon groups having from 2 to 15 carbon atoms. Illustrative of such alkenyl groups are 2-propenyl, hexenyl, octenyl, decenyl and the like.

As used herein the term "alkoxy" wherein the alkyl is 1 to 6 carbon atoms" refers to straiqht or branched chain ethers. Illustrative of such groups are methoxy, ethoxy, propoxy, butoxy, isopropoxy and the like.

As used herein the term "heteroaromatic ring" refers to ring compounds containing atoms of at least two different elements as ring members. These elements are selected from carbon, nitrogen, oxygen, or sulfur. Illustrative of such rings are pyridine, furan, pyrrole, thiophene, imidazole and oxazole.

Included within the embodiments of the present invention are the tautomeric forms of the described compounds, isomeric forms including geometric isomers, enantiomers and diastereoisomers, and the pharmaceutically acceptable salts thereof.

The term "pharmaceutically acceptable acid addition salt" refers to a salt prepared by contacting a compound of formula (I) with an acid whose union is generally considered suitable for human consumption. Examples of pharmacologically acceptable acid addition salts include but are not limited to the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

The compounds of formula I may be prepared in accordance with the following procedures.

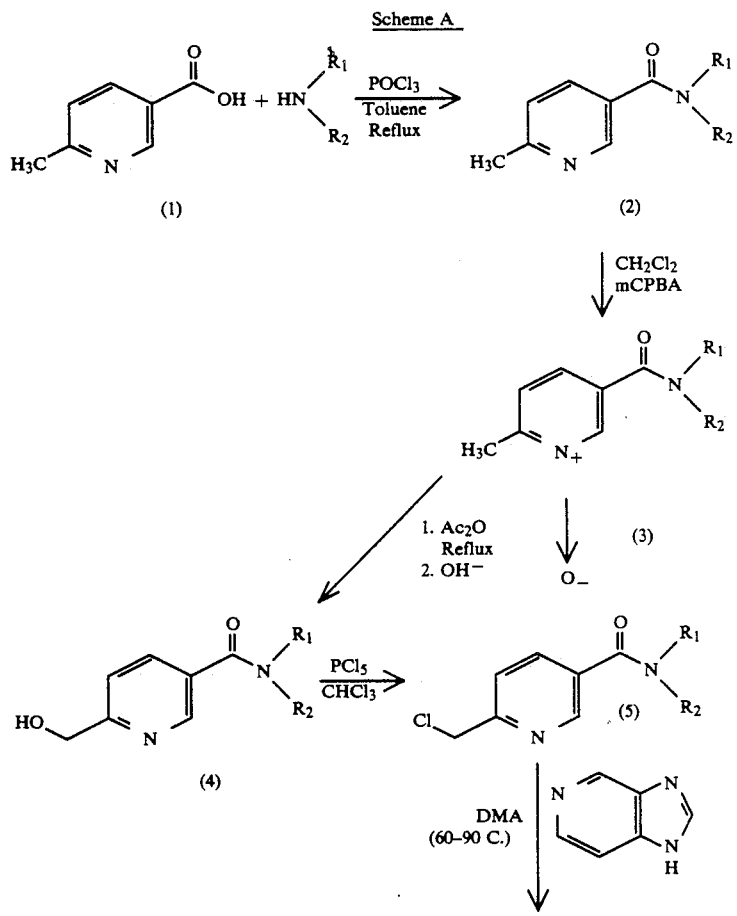

-continued

Scheme A

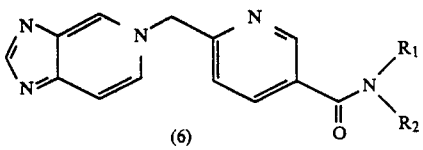

(6)

wherein $R_1$ and $R_2$ can each be hydrogen, straight or branched chain alkyl, cycloalkyl, phenyl or alkenyl. It is understood that these groups may be substituted by alkyl or halogen. It is further understood that the imidazopyridine may also be substituted as described earlier.

Thus a solution of 6-methyl nicotinic acid, 1 the amine and phosphorus oxychloride is refluxed in a solvent such as toluene for 6–10hr to give the N,N-dialkylpyridine carboxamide 2. The 6-methyl group of compound 2 is then converted to the hydroxy methyl derivative 4 in a three-step process involving oxidation (m-chloroperbenzoic acid, $CH_2Cl_2$, room temperature, 12–24hr), rearrangement (acetic anhydride, reflux) and hydrolysis (MeOH, potassium carbonate). Treatment of 4 with $PCl_5$ in chloroform (reflux≈18hr) gives the chloromethyl derivative 5 which is then coupled to the imidazopyridine (dimethyl acetamide, 40°–90° C.) to give the compound 6 after purification thru chromatography.

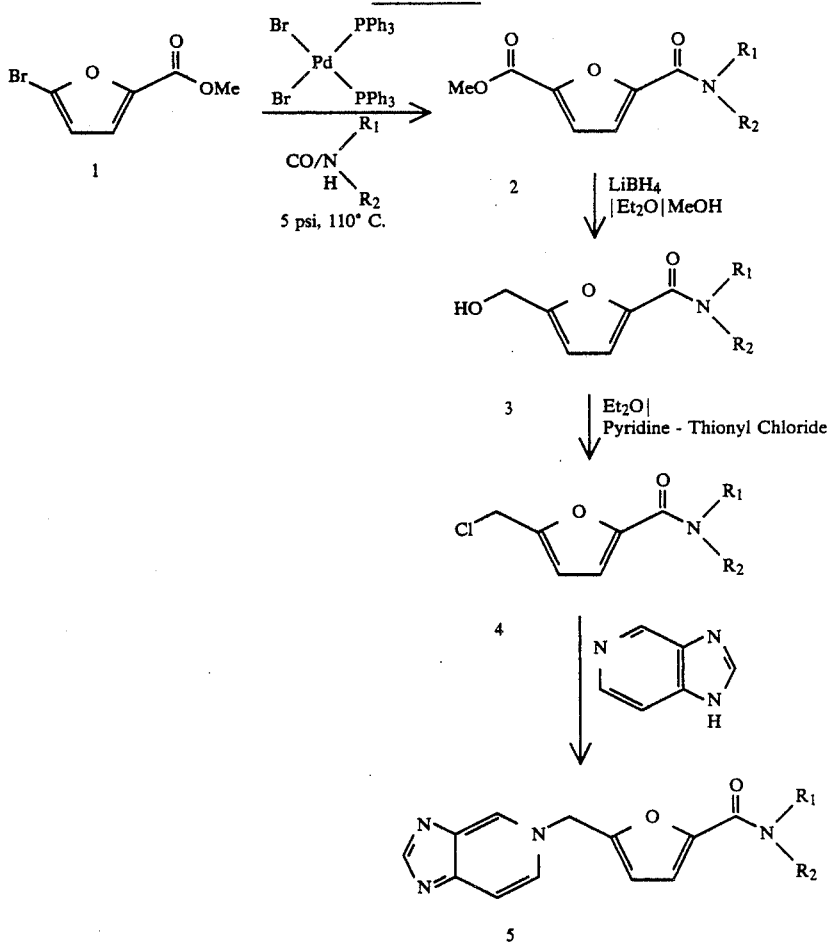

Scheme B wherein $R_1$ and $R_2$ are defined as in Scheme A.

Thus methyl 5-(N,N-dialkyl)carboxamido-2-furancarboxylate 2 is prepared from methyl 5-bromofurancarboxylate 1 by following the general methodology of carbonyl insertion reactions developed by a A. Schoenberg, L. Bartoletti, R. F. Heck, J. Org. Chem , 39, 3327 (1974). The methyl ester functionality is then converted to chloromethyl derivative 4 in a two step sequence involving - reduction ($LiBH_4$ ether/methanol, reflux) and chlorination (pyridine, thionyl chloride). Condensation of 4 with imidazopyridine gives the dehydrohalogenated product 5 after purification thru chromatography.

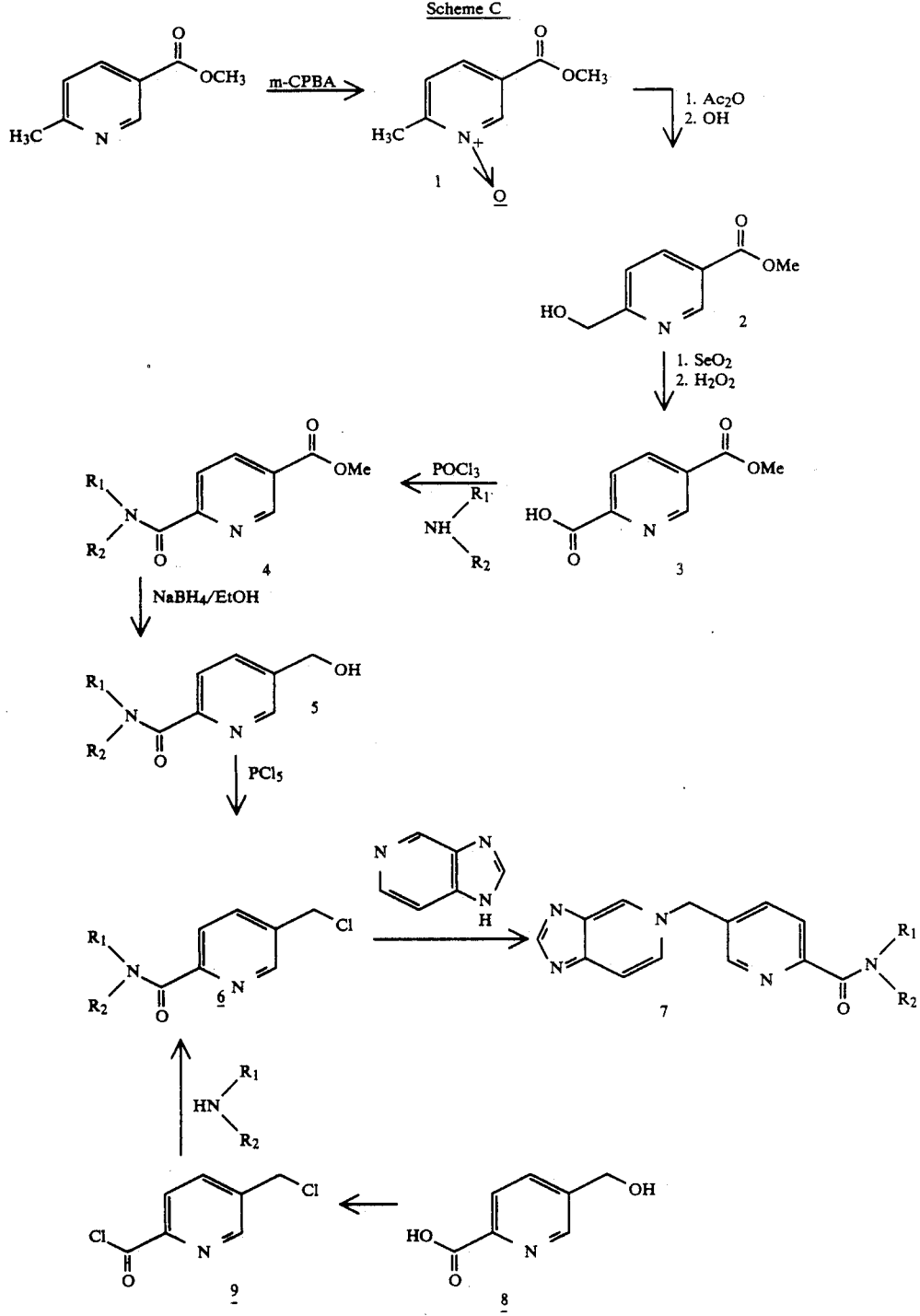

wherein $R_1$ and $R_2$ are defined as in Scheme A.

Thus the analog 7 in which the pyridine nitrogen is ortho to the amide group is prepared from methyl-6-methyl-nicotinate by functionalizing the 6-methyl to hydroxymethyl derivative 2 following the oxidation and rearrangement sequence described in Scheme A for the conversion of 2 to 4. The 6-hydroxymethyl group is then oxidized to 6-formyl and then to carboxylic acid by using reagents such as $SeO_2$ and $H_2O_2$ respectively as described in Davison, et al., J Med Chem, 26, 1282, 1983; Mastsumoto, I., Junge, Y. Chem Abstr 78, 1136100a; Chem Abstr. 78, 16049a The acid is converted to amide 4 by treatment with reagents such as phosphorus oxychloride and the amine. Reduction of the carbmethoxy group of 4 by reagents such as sodium borohydride or lithium borohydride following the procedure of Dawson, et. al J Med Chem 26, 1282 (1983) gives hydroxymethyl 5 which is converted to chloromethyl derivative 6 by reaction with $PCl_5$. The condensation of 6 with imidazopyridine (dimethylacetamide, 40°–90° C.) followed by purification thru chromatography gives 7.

Alternately the intermediate 6 is prepared from 5-hydroxymethyl picolinic acid 8, by conversion to the chloro derivative 9 using reagents such as PCl₅, POCl₃.

The reaction of amine selectively with acid chloride in solvents such as THF gives the desired amide 6. The intermediate 8 is easily prepared as described by Dawson et. al., J. Med. Chem 26, (1983).

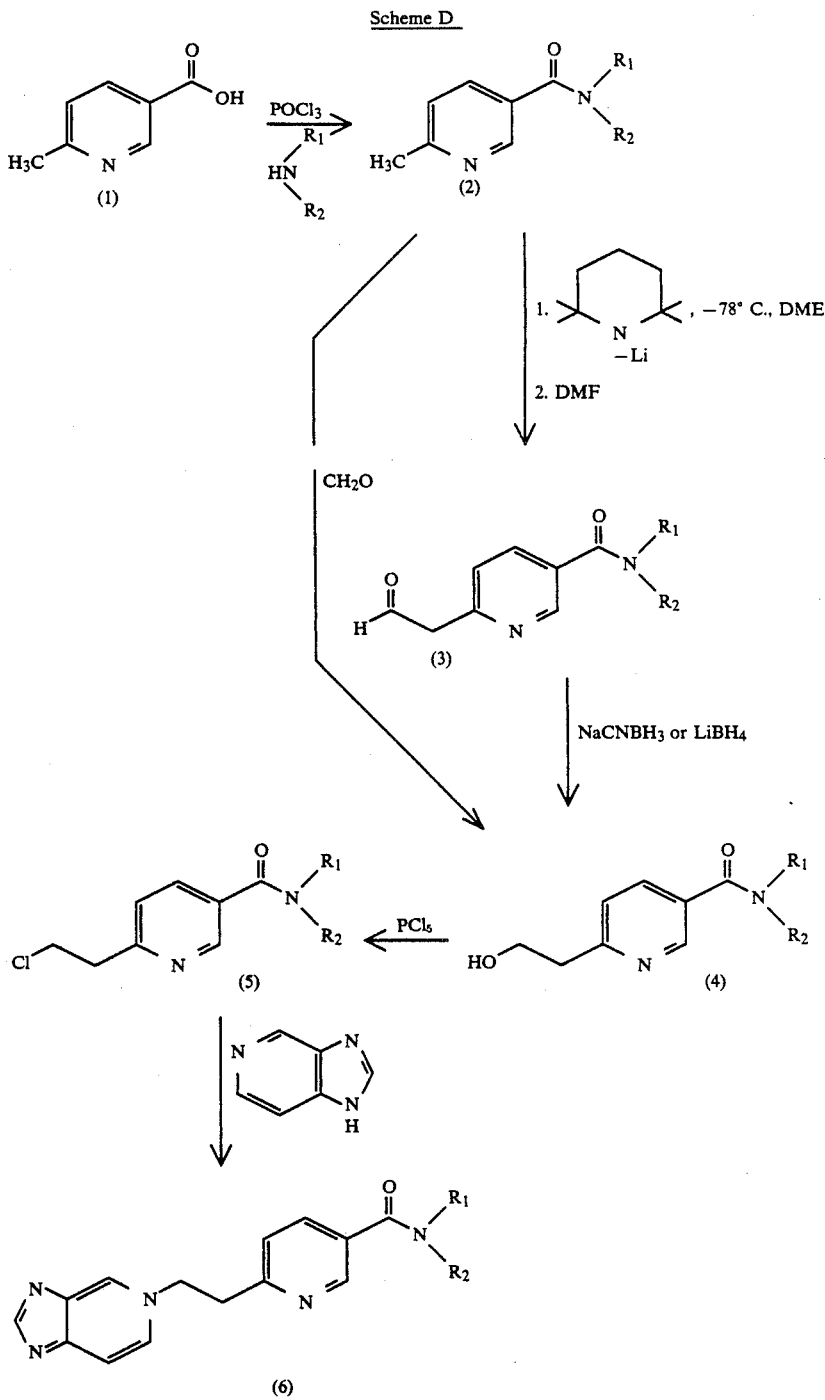

Scheme D wherein $R_1$ and $R_2$ are defined as in Scheme A.

Scheme D₁

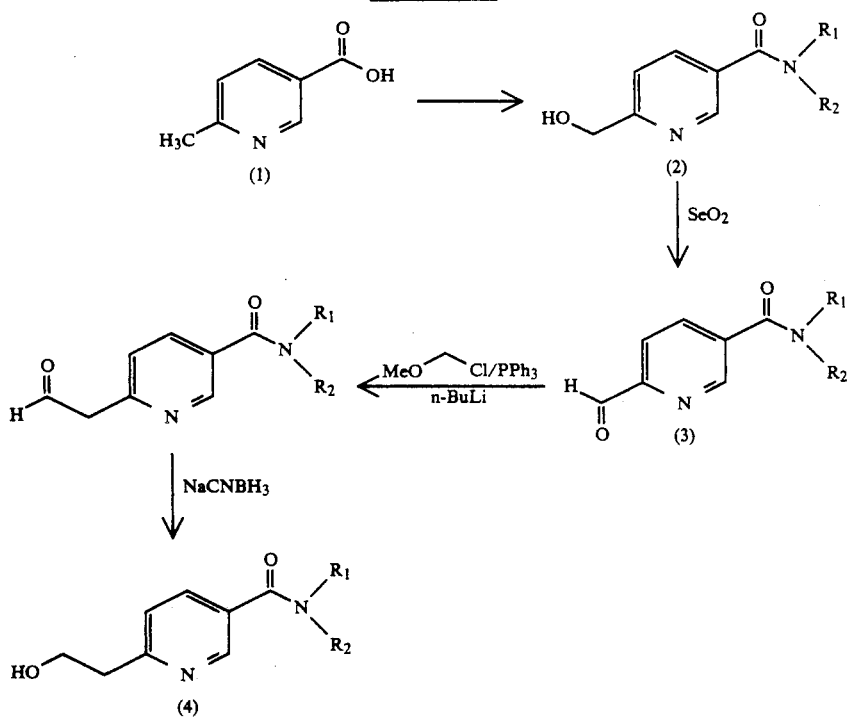

Thus intermediate 2 as prepared in Scheme A is lithiated with lithium tetramethyl piperidide at −78° C. according to the procedure of M. Watanabe et al. [Tetrahedron Letters 43, 5281(1987)]. Quenching this intermediate with dimethylformamide or formaldehyde gives the intermediates 3 or 4 respectively. Chlorination of 4 gives chloroethyl analog 5 which after condensation with imidazopyridine gives 6.

Scheme D₁

Alternately intermediate 4 in Scheme D is prepared from 2 (ref. intermediate 4 in Scheme A) by oxidation with reagents such as $SeO_2$ or $CrO_3$, Wittig homologation ($ClCH_2OMe$, PPhd 3, n-BuLi, 78° C.) and reduction (sodium cyanoborohydride).

Scheme E

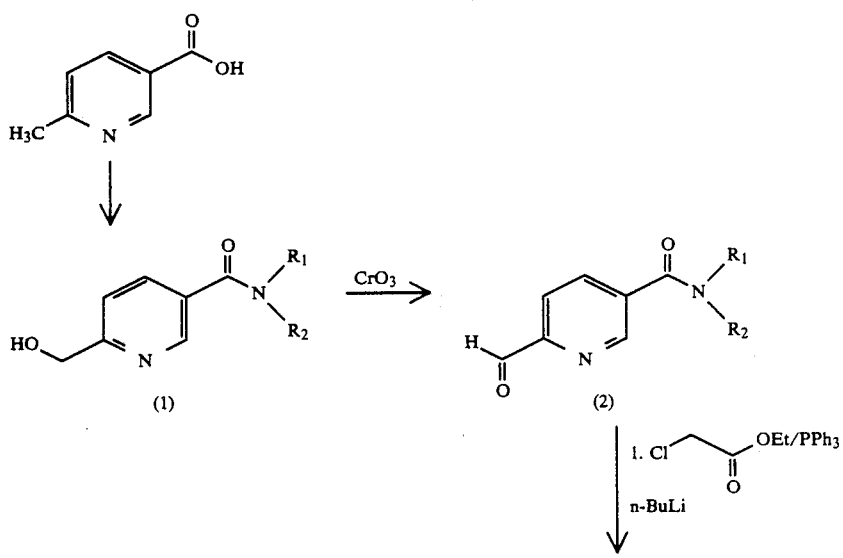

Scheme E

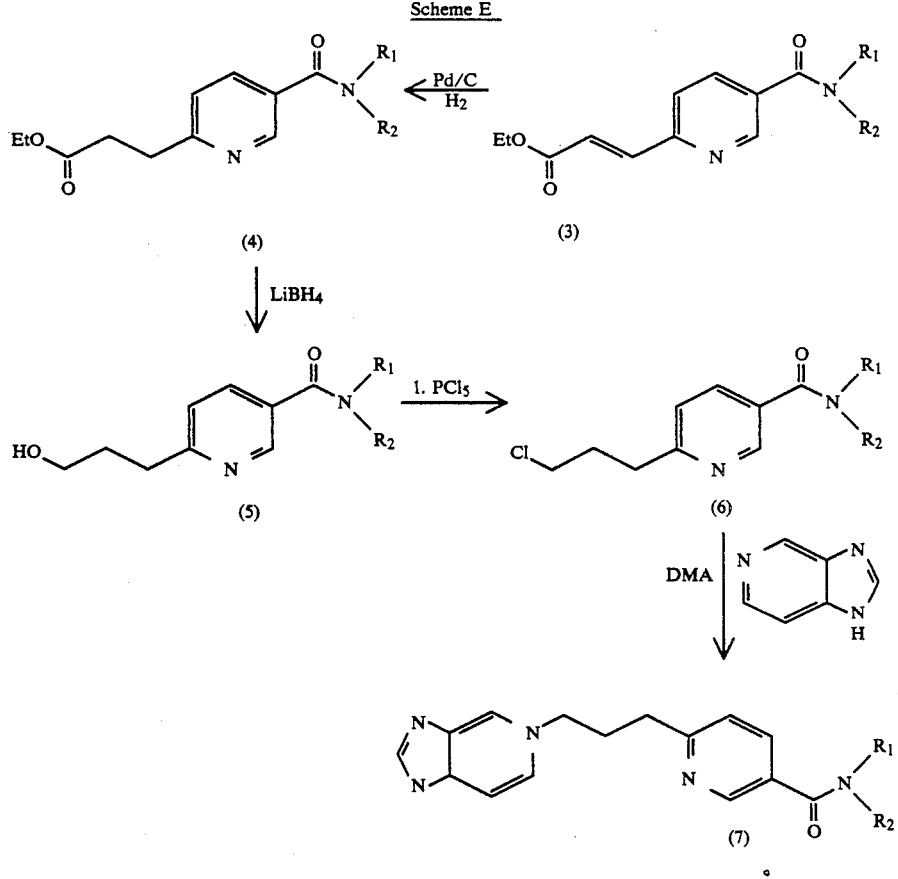

$R_1$ and $R_2$ are defined as in Scheme A.

Thus intermediate 2 obtained from 6-methyl nicotinic acid (ref. intermediate 3 Scheme $D_1$) is subjected to Wittig conditions (Br $CH_2CO_2Et$, $PPh_3$, n-BuLi) to give α, β- unsaturated ester 3 which on reduction (Pd/C, $H_2$) gives saturated ester 4. Ethyl ester in 4 is then reduced (LiBH$_4$) and converted to chloro derivative 5 using PCl$_5$. Condensation of 5 with imidazopyridine gives the coupled product after purification.

Scheme F

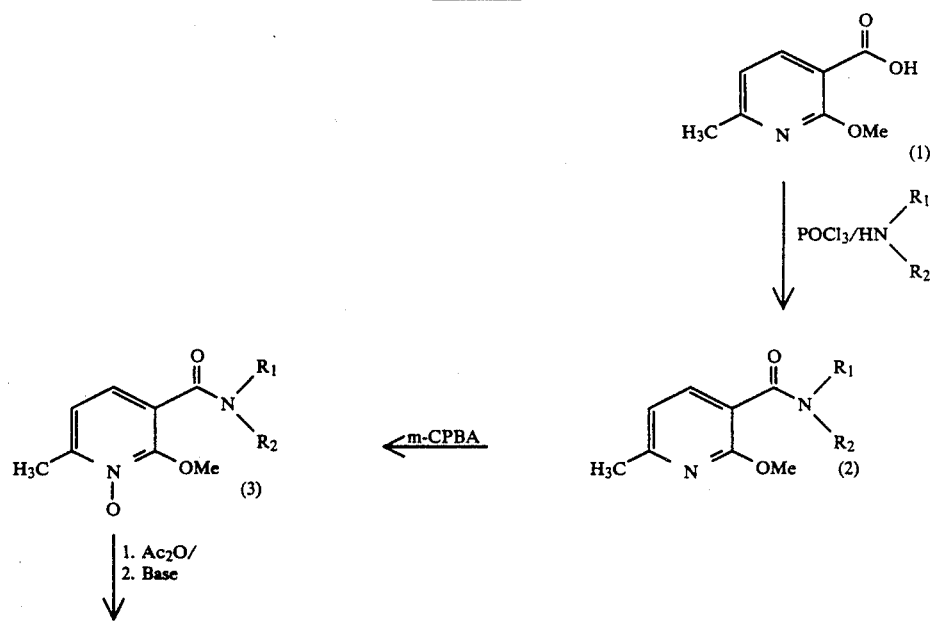

-continued

Scheme F

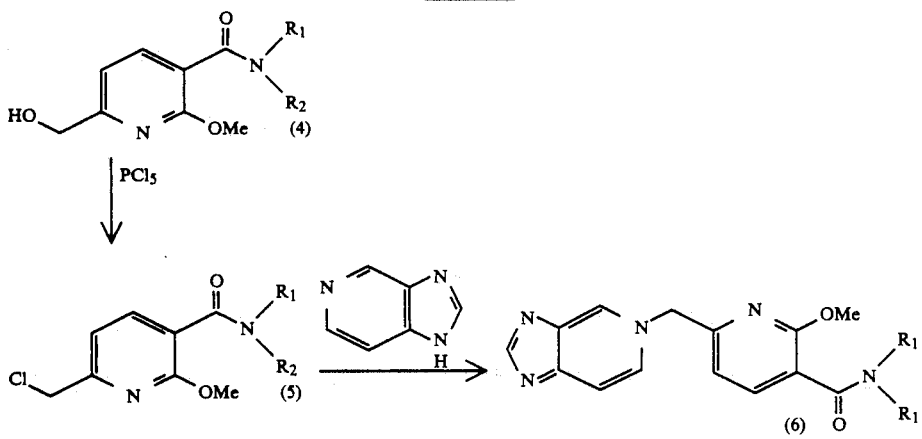

R₁ and R₂ are defined as in Scheme A.

Thus 2-methoxy-6-methyl-nicotinic acid 1, prepared following the procedure of P. Beak et al., J. Org Chem. 45, 1354(1980), is converted to the amide 2 using POCl₃, HNR₁R₂. Elaboration of 6-methyl to hydroxy methyl 4 is carried out as illustrated in Scheme A. Treatment of 4 with PCl₅ gives the chloro derivative 5 which condenses with imidazopyridine to give 6.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of compound (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, compound (I) may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may for example be administered intravascularly, orally, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 250 mg preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os , the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

Dosage levels of the order from about 1 mg to about 100 mg per kilogram of body weight per day are useful in the treatment of the above-indicated conditions (from about 50 mg to about 5 mgs. per patient per day). For example, inflammation is effectively treated and antipyretic and analgesic activity manifested by the administration from about 25 to about 75 mg of the compound per kilogram of body weight per day (about 75 mg to about 3.75 gm per patient per day). Preferably, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 95 mg of active agent compounded with an appropriate and convenient amount of carrier material which may vary from about 5 to 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to further illustrate the present invention and not to limit the invention in spirit or scope. In the Examples, all parts are parts by weight unless otherwise expressly set forth.

PREPARATION OF STARTING MATERIAL

EXAMPLE A

Preparation of 6-Methyl-N,N-dicyclopentylnicotinamide

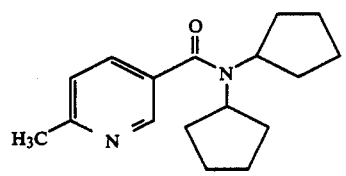

To a suspension of 6-methylnicotinic acid (1.37 g, 10 mmol) in toluene (10 ml), N,N-dicyclopentylamine (1.84 g, 12 mmol) was added To the homogenous solution obtained, phosphorus oxychloride (0.23 mL, 12 mmol) was injected in dropwise fashion. The reaction mixture was then immersed in an oil-bath at 130° C. and refluxed for 8 h. The reaction flask was cooled and stirred at room temperature. After 16h, the reaction was quenched with water and extracted in ethyl acetate. The organic layer was successively washed with aq. potassium carbonate, water and brine. After drying (MgSO$_4$), the solvent was removed. The crude product (2.5 g) was chromatographed (silica gel, ethyl acetate/acetonitrile 100/1.5) to give the title compound (1.2 g, 44%). IR (KBr)1625, 1590, 1450, 1430, 1375, 1340, 1290, 1130, 840, 750 cm$^{-1}$; $^1$H NMR (CDCl$_3$) 1.4–2.35 (m, 16H), 2.57 (s, 3H), 3.6–3.9 (m,2H), 7.17 (d, J=8 Hz, 1H), 7.6 (dd,J=3,8 Hz, 1H), and 8.5 ppm (d,J=3 Hz,1H).

EXAMPLE B

Preparation of 6-Methyl-N,N-dicyclopentylnicotinamide-N-oxide

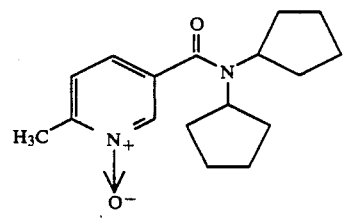

To a solution of the product of Example A (0.5 g, 1.84 mmol) in methylene chloride (15 mL), m-chloroperbenzoic acid (485 mg. 85%, 2.38 mmol) was added. After stirring at room temperature for 18 h, the solvent was removed under reduced pressure. The colorless liquid obtained was then chromatographed (silica gel, methylene chloride/methanol 94/6) to give the title compound (460 mg, 87%). $^1$H NMR (CDCl$_3$) 1.4–2.2(m, 16H), 2.53 (s, 3H), 3.6–3.85 (m,2H), 7.16(dd, J=3, 8 Hz, 1H), 7.25 (d,J=8 Hz, 1H), and 8.24 ppm (d, J=3 Hz, 1H).

EXAMPLE C

Preparation of 6-Hydroxymethyl-N,N-dicyclopentylnicotinamide

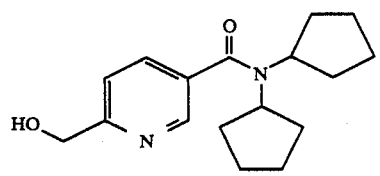

A solution of the product of Example B (5 4 g, 18.75 mmol) in acetic anhydride (20 mL) was refluxed for 3h. After cooling, the solvent was removed under reduced pressure. The reaction was diluted with ethyl acetate and washed successively with aq. potassium carbonate, water and brine. After drying over MgSO$_4$, the organic layer was filtered and concentrated to give the dark orange liquid (5.79 g). The residue was redissolved in methanol (100 mL) and saturated aq. potassium carbonate (25 mL) was added. The mixture was heated at 50°–60° C. for 16h. The reaction was cooled and neutralized with 1N HCl. Methanol was removed and the residue redissolved in methylene chloride. The organic layer was washed (water and brine), dried (MgSO$_4$) and concentrated to give 4.5 g of the crude product.

After chromatography 1.62 g (29%) of the title compound was isolated ¹H NMR (CDCl₃)1.35–2.4(m,16H), 3.55–3.95(m,2H) 4.3 (t, J=5 Hz,1H; exchanges with D20), 4.75 (d,J=5 Hz, 2H), 7.3 (d,J=8 Hz, 1H), 7.65 (dd,J=3,8 Hz, 1H), 8.5 ppm (d,J=3 Hz, 1H); 13C NMR (CDCl₃) 168, 160.3, 145.8, 134.7, 132.8, 120, 77.64, 77, 76.4, 64.2, 64.17, 64.12, 30.1, 25.3, 25.2

EXAMPLE D

Preparation of 6-Chloromethyl-N,N-dicyclopentylnicotinamide

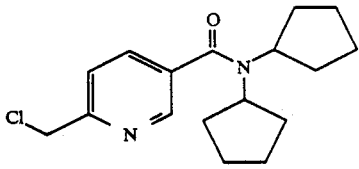

To a solution of the title product of Example C (1.44 g, 5 mmol) in chloroform (30 mL), phosphorus pentachloride (1.04, 5 mmol) was added. The contents were immersed in an oil-bath at 70° C. and the temperature raised to reflux. After 18h, the pinkish colored reaction solution was cooled to room temperature. The reaction was diluted with water (75 mL) and solid potassium carbonate (2.2 g) added. The contents were stirred for about 10 min until no more effervescence was observed. More water (100 mL) was added and the reaction solution extracted with methylene chloride. The organic layer was separated, dried (MgSO₄) and filtered. After removal of solvent, 1 6 g of the title product was isolated as an off-white solid. The compound was used in Example 1 without any further purification. ¹H NMR (CDCl₃) 1,2–2.2 (m, 16H), 3.6–3.9 (m, 2H), 4.7 (s, 2H), 7.53 (d,J=8 Hz, 1H), 7.74 (dd,J=3,8 Hz, 1H), and 8.56 ppm (d,J=3 Hz, 1H).

EXAMPLE E

Preparation of Methyl 5-Bromo 2-furancarboxylate

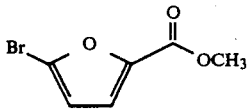

To a solution of 5-bromofuroic acid (2 g, 10.47 mmol) in methanol (100 mL), conc. sulfuric acid (0.1 mL) was added and the contents were refluxed under argon. After 18 h, the solvent was removed under reduced pressure and the residue diluted with ethyl acetate. The organic layer was successively washed with aq. potassium carbonate, water and brine. After drying (MgSO₄) and filtering, the filtrate was concentrated to give the title compound (1.1 g, 54%) which was used in Example F without any further purification; ¹H NMR (CDCl₃) 3.9 (s, 3H), 6.47 (d,J=4 HZ, 1H), 7.13 ppm (d,J=4 Hz, 1H).

EXAMPLE F

Preparation of Methyl 5-(N-methyl,N-cyclohexyl)carboxamido-2-furancarboxylate

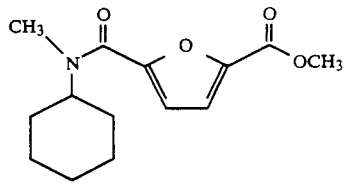

Methyl 5-bromo-2-furancarboxylate of Example E (976 mg, 4.46 mmol) was dissolved in N-methyl, N-cyclohexylamine (2 mL) in a 6 ounce aerosol reaction vessel. The reaction mixture was flushed with carbon monoxide several times and then maintained at delivery pressure of 2 psi. The temperature of the reaction vessel was raised to 100° C. The catalyst trans dibromobistriphenylphosphine palladium (51 mg, 0.06 mmol), suspended in amine (2 mL) was added via syringe. Gas absorption changes and times were recorded until the theoretical amount of gas was absorbed. After the reaction was over (4 h), the carbon monoxide was vented and the black thick residue was triturated with ether and filtered.

The ethereal layer was washed with 10% HCl (100 mL), water and brine. After drying (MgSO₄) and concentration, the title compound (540 mg, 45%) obtained was used in Example G without further purification. ¹H NMR (CDCL₃) 1.0–1.9(m,13H), 4–4.1 and 4.35–4.5(m.1H), 3.85(s,3H), 7.03(d, J=4 Hz,1H), 7.2 ppm (d,J=4 Hz,1H).

\* The reaction conditions used above are based on general methodology of carbonyl insertion reactions developed by A. Schoenberg, L. Bartoletti, R. F. Heck, J. Org. Chem., 39 3327 (1974).

EXAMPLE G

Preparation of 5-(N-Methyl,N-cyclohexyl)carboxamido furfuryl alcohol

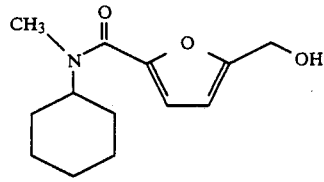

To a solution of the product of Example F (600 mg, 2.26 mmol) in ether (30 mL), methanol (0.14 mL) was added followed by dropwise addition of lithium borohydride (3.4 mL, 2M solution in THF, 3.4 mmol). The reaction flask was immersed in an oil-bath preheated at 50° C. and refluxed under argon. After 2 hr, the reaction mixture was cooled to room temperature and poured over ice. 1N Hydrochloric acid (100 mL) was added and product extracted in ether. The ethereal layer was washed with water and brine. After drying (MgSO₄) and concentration, the crude product (410 mg) was chromatographed (silica gel, ethyl acetate/acetonitrile 100/1.5) to give the title compound (240 mg, 45%) as a white solid. ¹H NMR (CDCl₃) 1.05–2.2(m, 13H), 2.9–3.15 (brs, 1H), 3.5–4.1 (m, 1H), 4.63 (s,2H), 6.33 (d,J=4 Hz, 1H), 6.8 ppm (d, J=4 Hz, 1H)

EXAMPLE H

Preparation of 5-(N-Methyl,N-cyclohexyl)carboxamido-furfuryl chloride

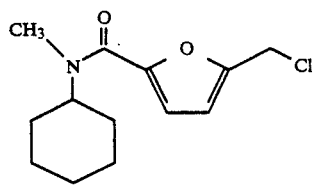

To a cold solution (0° C.) of the product of Example G (300 mg, 1.26 mmol) in ether (40 mL), pyridine (0.122 mL, 1.5 mmol) was added and the solution stirred under argon. A solution of thionyl chloride (0.138 mL. 1.9 mmol) in ether (5 mL) was cautiously added over 10 min. The reaction was stirred at 0°–10° C. for 20 min and then at room temperature for 3 hr. TLC examination of the reaction showed about 70% conversion. More thionyl chloride (0.1 mL) was added and the reaction solution stirred for additional 1 h. Ether was removed and the residue redissolved in ethyl acetate. After successively washing with aq. potassium carbonate, water and brine, the organic layer was dried (MgSO$_4$) and concentrated. The title compound (290 mg, 90%) obtained as white solid was used in Example 2 without further purification. $^1$H NMR (CDCl$_3$) 1.05–1.95(m, 13H), 3.9–4.4 (m, 1H), 4.57 (s, 2H), 6.42(d, J=4 Hz, 1H), 6.87 ppm (d,J=4 Hz, 1H).

EXAMPLE I

Preparation of Methyl 5-(N-cyclopentyl,N-cyclohexyl) carboxamido 2-furancarboxylate

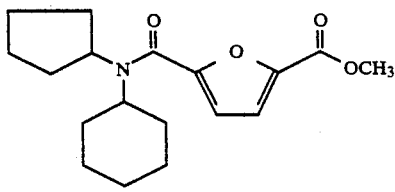

Methyl 5-bromo-2 furancarboxylate (1 g,4.56mmol) was dissolved in N-cyclopentyl, N-cyclohexylamine (2 mL) in a 6 ounce aerosol reaction vessel. The reaction mixture was flushed with carbon monoxide several times and then maintained at delivery pressure of 5psi. The temperature of the reaction vessel was raised to 100° C. The catalyst trans-dibromobistriphenylphosphine palladium (104 mg, 0.13 mmol), suspended in amine (2 mL) was added via syringe. Gas absorption changes and times were recorded until theoretical amount of gas was absorbed. After the reaction was over (72 hr), the carbon monoxide was vented and the black thick residue was triturated with ether and filtered. The etheral layer was washed with 10% HCl (100 mL), water and brine. After drying (MgSO$_4$) and concentration, the crude product (1.01 g) was chromatoqraphed to give the title product (400 mg, 29%). $^1$H NMR(CDCl$_3$)1.0–2.2(m,18H), 3.15–3.9(m, 2H), 3.85(s, 3H), 6.92(d,J=4 Hz, 1H), 7.18 ppm (d,J=4 Hz, 1H).

EXAMPLE J

Preparation of 5 (N-cyclopentyl,N-cyclohexyl)carboxamidofurfury alcohol

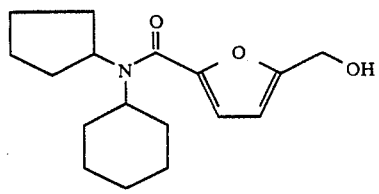

To a solution of the product of Example I (1.1 g, 3.45 mmol) in ether (60 mL), methanol (0.22 mL) was added followed by dropwise addition of lithium borohydride (2.8 mL, 2M solution in THF, 5.6 mmol). The reaction flask was immersed in an oil-bath preheated at 50° C. and refluxed under argon. After 2.5 hr, the reaction mixture was cooled to room temperature and poured over ice. 1N Hydrochloric acid (100 mL) was added and product extracted in ether. The ethereal layer was washed with water and brine. After drying (MgSO$_4$) and concentration, the crude product (940 mg) was chromatoqraphed (silica gel, ethyl acetate/acetonitrile 100/1.5) to give the title product (910 mg, 91%) as white solid. 1H NMR (CDCl$_3$) 1.05–2.2(m, 18H), 2.5–2.65(brs, 1H), 3.5–3.95(m, 2H), 4.63(s, 2H), 6.33 ppm (d, J=4 Hz, 1H), and 6.7 ppm (d, J=4 Hz, 1H).

EXAMPLE K

Preparation of 5-(N-Cyclopentyl,N-cyclohexyl) carboxamido-furfuryl chloride

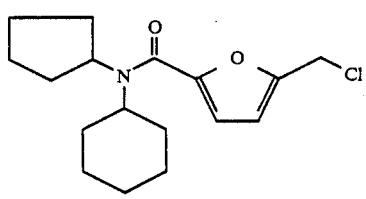

To a cold solution of the product of Example J (0° C.)(900 mg, 3.09 mmol) in ether (60 mL), pyridine (0.3 mL, 3.7 mmol) was added and solution stirred under argon. A solution of thionyl chloride (0.49 mL, 4.64 mmol) in ether (5 mL) was cautiously added over 15 min.

The reaction was stirred at 0°–10° C. for 20 min and then at room temperature for 3 hr. The solvent was removed and the residue redissolved in ethyl acetate. After successively washing with aq. potassium carbonate, water and brine, the organic layer was dried (MgSO$_4$) and concentrated. The title product (750 mg, 79%) was obtained as a white solid. $^1$H NMR (CDCl$_3$) 1.05–2.2(m, 18H), 3.45–3.9(m, 2H), 4.57(s, 2H), 6.42(d, J=4 Hz, 1H), and 6.77 ppm (d, J=4 Hz, 1H).

PREPARATION OF FINAL PRODUCTS

EXAMPLE 1

Preparation of
N,N-dicyclopentyl-6-(5H-imidazo[4,5-c]pyridin-5-yl-methyl)-3-pyridinecarboxamide

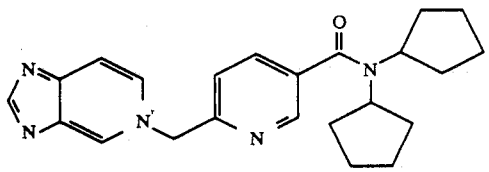

To a stirred solution of imidazopyridine (540 mg, 4.5 mmol) in dimethylacetamide (100 mL) under argon, the product of Example D (1.6 g,) was added in one portion. The reaction temperature was slowly raised to 80°–85° C. and was stirred for 60 h. The reaction flask was cooled to room temperature and the solvent was removed under reduced pressure at <45° C. The residue obtained was triturated with excess of dry ether and filtered.

The crude product (2.61 g) was chromatographed (silica gel, $CH_2Cl_2:MeOH:NH_4OH::90:10:1$) to give pure alkylated product (940 mg, 54%) which was recrystallized from ethyl acetate/acetonitrile to give the title compound as a pure white solid, mp 227°–28° C., $^1H$ NMR ($CD_3OD$), 1.4–1.95 (m, 16H), 3.65–3.9 (m, 2H), 5.88 (s, 2H), 7.54 (d,J=8 Hz, 1H), 7.8–7.86 (m, 2H), 8.24 (dd,J=3,8 Hz, 1H), 8.44 (s, 1H), 8.5 (d, J=3 Hz, 1H), and 9.07 ppm (d,J=3 Hz, 1H). Anal. calcd. for $C_{23}H_{27}N_5O$: C, 70.92, H, 6.94, N, 17.99. Found C, 70.64, H, 6.97, N, 17.83.

EXAMPLE 2

Preparation of
N-cyclohexyl-5-[(5H-imidazo[4,5-c]pyridin-5-yl)methyl]N-methyl-2-furancarboxamide

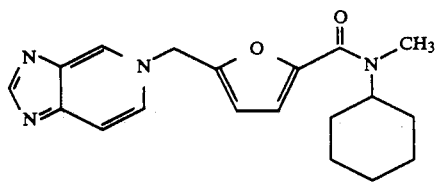

To a stirred solution of imidazopyridine (150 mg, 1.25 mmol) in dimethylacetamide (30 mL) under argon, furfuryl chloride (product of Example H) (320 mg. 1.25 mmol) was added in one portion. The reaction temperature was slowly raised to 75° C. and was stirred for 60 hr. The reaction flask was cooled to room temperature and the solvent was removed under reduced pressure at <45° C. The residue obtained was triturated with excess of dry ether and filtered. The crude product (410 mg) was chromatographed (silica gel, $CH_2Cl_2:MeOH:NH_4OH::90:10:1$) to give the title compound (265 mg, 65%) as white solid, mp 189–90° C., $^1H$ NMR ($CDCl_3$) $^1H$ NMR ($CDCl_3$) 0.85 –1.9(m, 13H), 3.6–3.8 & 4.3–4.45(m, 1H), 5.62 (s, 2H), 6.62 (brs, 1H), 6.82 (brs, 1H), 7.73 (dd, J=7 Hz, 1H), 7.85 (dd, J=3,7 Hz, 1H), 8.57 (s, 1H), 8.8 ppm (s, 1H), Anal calcd. for $C_{19}H_{22}N_4O_2$ $0.5H_2O$: C, 65.70,H,6.62, N, 16.11. Found: C, 65.65, H, 6.71, N, 16.06.

EXAMPLE 3

Preparation of
N-cyclohexyl-N-cyclopentyl-5-(5H-imidazo[4,5-c]pyridin-5-yl-methyl)-2-furancarboxamide

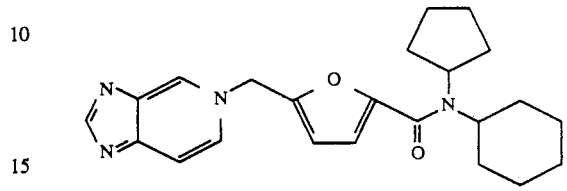

To a stirred solution of imidazopyridine (256 mg, 2.15 mmol) in dimethylacetamide (25 mL) under argon, the product of Example K. (700 mg, 2.26 mmol was added in one portion. The reaction temperature was slowly raised to 75° C. and was stirred for 60 hr. The reaction flask was cooled to room temperature and the solvent was removed under reduced pressure at <45° C. The residue obtained was triturated with excess of dry ether and filtered. The crude product (920 mg) was chromatoqraphed on silica gel, using $CH_2Cl_2:MeOH:NH_4OH$ (90:10:1) to give the title compound (790 mg, 93%) as a white solid, mp 189°–90° C. $^1H$ NMR($CDCl_3$)0.85–2.2(m, 18H), 3.2–3.85(m, 2H), 5.49(s, 2H), 6.62(d, J=4 Hz,1H), 6.74(d, J=4 Hz,1H), 7.76(dd,J=3,7 Hz, 1H), 7.82(d,J=7 Hz, 1H), 8.6(d, J=3 Hz, 1H), and 8.62 ppm (s, 1H). Anal calcd. for $C_{23}H_{28}N_4O_2$: C,70.40,H, 7.14,N,14.28. Found:C, 70.15,H,7.25,N,14.19.

EXAMPLE 4

Preparation of
N-cyclohexyl-5-[(imidazo[4,5-c]pyridin-5-yl)methyl]-N-(1-methylethyl)-2-furancarboxamide

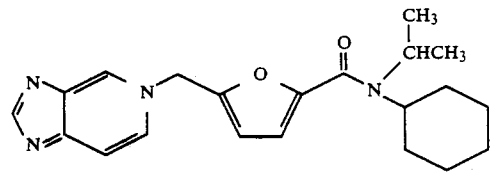

To a stirred solution of imidazopyridine in dimethylacetamide under argon, N-isopropyl, N-cyclohexyl5-(chloromethyl) 2-furancarboxamide is added in one portion. The reaction temperature is slowly raised to 75° C. and stirred for 24–60 hr. The reaction flask is cooled to room temperature and the solvent is removed under reduced pressure at <45° C. The residue is triturated with excess of dry ether and filtered. The crude product is chromatographed on silica gel using mixtures of $CH_2Cl_2:MeOH:NH_4OH$) to give the title compound.

EXAMPLE 5

Preparation of
N-cyclohexyl-6-(5H-imidazo[4,5-c]pyridin-5-yl-methyl)-N-(1-methylethyl)-3-pyridinecarboxamide

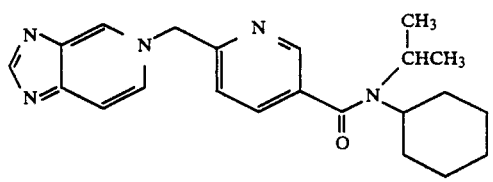

To a stirred solution of imidazopyridine in dimethylacetamide under argon, N-isopropyl, N-cyclohexyl 2 (chloromethyl)-5-pyridinecarboxamide is added in one portion. The reaction temperature is slowly raised to 80°-85° C. and stirred for 24-60hr. The reaction flask is cooled to room temperature and the solvent is removed under reduced pressure at <45° C. The residue is triturated with excess of dry ether and filtered. The crude product is chromatographed on silica gel using mixtures of CH₂Cl₂:MeOH:NH₄OH to give the title compound.

EXAMPLE 6

Preparation of
6-(5H-imidazo[4,5-c]pyridin-5-yl-methyl)-N-(1-methylethyl)-N-phenyl-3-pyridinecarboxamide

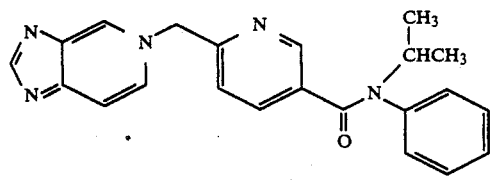

To a stirred solution of imidazopyridine in dimethylacetamide under argon, N-isopropyl, N-phenyl-2-(chloromethyl)-5-pyridinecarboxamide is added in one portion. The reaction temperature is slowly raised to 80°-85° C. and stirred for 24-60 hr. The reaction flask is cooled to room temperature and the solvent is removed under reduced pressure at <45° C. The residue is triturated with excess of dry ether and filtered. The crude product is chromatographed on silica gel using mixtures of CH₂Cl₂:MeOH:NH₄OH to give the title compound.

EXAMPLE 7

Preparation of
N,N-dicyclopentyl-5-(5H-imidazo[4,5-c]pyridin-5-yl-methyl-2-methoxy-3-pyridinecarboxamide

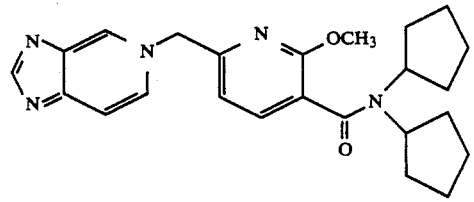

To a stirred solution of imidazopyridine in dimethylacetamide under argon, N,N dicyclopentyl-6-(chloromethyl)-2-methoxy-3-pyridine carboxamide is added in one portion. The reaction temperature is slowly raised to 80°-85° C. and stirred for 60 hr. The reaction flash is cooled to room temperature and the solvent is removed under reduced pressure at <45° C. The residue is triturated with excess of dry ether and filtered. The crude product is chromatographed on silica gel, using mixtures of CH₂Cl₂:MeOH:NH₄OH to give the title compound.

EXAMPLE 8

Preparation of
N,N-dicyclopentyl-6-[3-(5H-imidazo[4,5-c]pyridin-5-yl)propyl]-3-pyridinecarboxamide

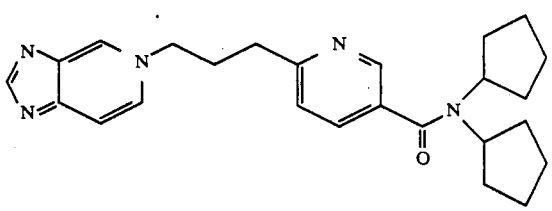

To a stirred solution of imidazopyridine in dimethylacetamide under argon, N,N-dicyclopentyl-2-(3-chloropropyl)-5-pyridinecarboxamide is added in one portion. The reaction temperature is slowly raised to 80°-85° C. and stirred for 24-60 hr. The reaction flask is cooled to room temperature and the solvent is removed under reduced pressure at <45° C. The residue is triturated with excess of dry ether and filtered The crude product is chromatographed on silica gel using mixtures of CH₂Cl₂:MeOH NH₄OH to give the title compound.

EXAMPLE 9

Preparation of
N,N-dicyclopentyl-6-[2-(5H-imidazo[4,5-c]pyridin-5-yl)ethyl]-3-pyridinecarboxamide

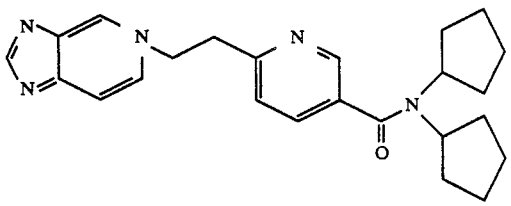

To a stirred solution of imidazopyridine in dimethylacetamide under argon, N,N-dicyclopentyl-2(2-chloroethyl)-5-pyridinecarboxamide is added in one portion. The reaction temperature is slowly raised to 80°-85° C. and stirred for 24-60 hr. The reaction flask is cooled to room temperature and the solvent is removed under reduced pressure at <45° C. The residue is triturated with excess dry ether and filtered. The crude product is chromatographed on silica gel using mixtures of CH₂Cl₂:MeOH:NH₄OH to give the title compound.

EXAMPLE 10

Preparation of
N,N-dicyclopentyl-6-(5H-imidazo[4,5-c]pyridin-5-yl methyl]-3-pyridinecarboxamide

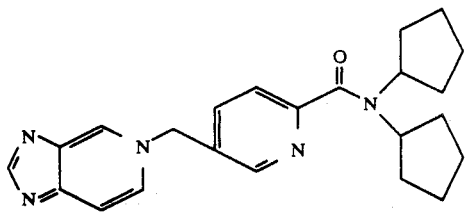

To a stirred solution of imidazopyridine in dimethylacetamide under argon, N,N-dicyclopentyl-5-(chloromethyl)-2-pyridinecarboxamide is added in one portion. The reaction temperature is slowly raised to 80°-85° C. and stirred for 24-60 hr. The reaction flask is cooled to room temperature and the solvent is removed under reduced pressure at <45° C. The residue is triturated with excess dry ether and filtered. The crude product is chromatographed on silica gel using mixtures of $CH_2Cl_2$:MeOH:$NH_4OH$ to give the title compound.

EXAMPLE 11

Preparation of
N-Ethyl,N-cyclopentyl-6-[5H-(imidazo[4,5-c]pyridin-5-yl) methyl]-3-pyridinecarboxamide

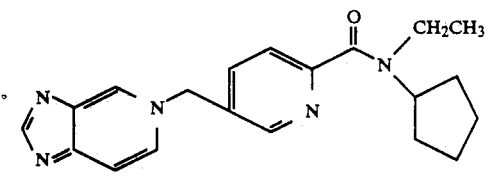

To a stirred solution of imidazopyridine in dimethylacetamide under argon, N-ethyl, N-cyclohexyl-6(chloromethyl)-3-pyridinecarboxamide is added in one portion. The reaction temperature is slowly raised to 80°-85° C. and stirred for 24-60 h. The reaction flask is cooled to room temperature and the solvent is removed under reduced pressure at <45° C. The residue obtained is triturated with excess dry ether and filtered. The crude product is chromatographed on silica gel using mixtures of $CH_2Cl_2$:MeOH: $NH_4OH$ to give the title compound.

EXAMPLE 12

Preparation of 5-[5-[(N-2-Methallyl,N-cyclohexyl) carboxamido)-furfuryl]imidazo[4,5-c]pyridine

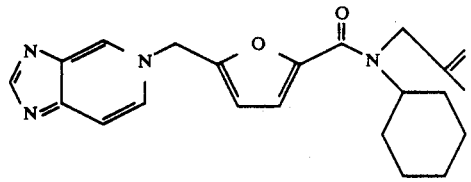

To a stirred solution of imidazopyridine in dimethylacetamide under argon, N-2-methallyl, N-cyclohexyl 5-(chloromethyl)-2 furanocarboxamide is added to one portion. The reaction temperature is slowly raised to 75° C. and is stirred for 24-60 h. The reaction flask is cooled to room temperature and the solvent is removed under reduced pressure at <45° C. The residue is triturated with excess dry ether and filtered. The crude product is chromatographed on silica gel using mixtures of $CH_2Cl_2$:MeOH:$NH_4$ to give the title compound.

EXAMPLE 13

PAF-induced platelet aggregation and secretion: Washed, [$^3$H]serotonin labeled rabbit platelets were prepared as previously described in COX, C. P , J. LINDEN and S. I. SAID: VIP elevates platelet cyclic AMP (cAMP) levels and inhibits in vitro platelet activation induced by platelet-activating factor (PAF). Peptides 5:25-28, 1984, and maintained in an atmosphere of 5% $CO_2$ at 37° C. until used in the bioassay. Aliquots of platelets ($2.5 \times 10^8$/ml) were incubated with either an antagonist of PAF or the appropriate vehicle for 60 sec prior to the addition of PAF (0.2 nM to 0.2 $\mu$M). Aggregation was continuously monitored on a strip-chart recorder and recorded as the height of the tracing at 60 sec after the addition of PAF. Secretion of [$^3$H] serotonin was measured in a sample of the platelet suspension removed at 60 sec after the addition of PAF. The percent inhibition of aggregation and secretion was calculated by comparing antagonist-treated platelets with the appropriate vehicle-treated control platelets. Each combination of antagonist and PAF was repeated using different platelet preparations. $IC_{50}$ values were determined by inspection of the dose-response curves.

EXAMPLE 14

Inhibition of $^3$H-PAF Binding to Human Platelet Membrane Receptors

Receptor Preparation: Ten units of in-dated human packed platelets, each containing 45-65 ml platelet rich-plasma, were purchased from a commercial blood bank. Disposable plasticware was used throughout for receptor preparation. The units were pooled and a 1 ml aliquot was removed for determination of platelet concentration, using a Coulter Counter. The remaining platelet rich plasma was dispensed into 50 ml conical tubes and centrifuged at room temperature for 15 minutes at 3000 RPM ($2300 \times g$). Plasma was decanted and the platelets were resuspended in 35 ml of buffer (10 mM Trizma 7.0, 2 mM EDTA (dipotassium salt), and 150 mM KCl) and transferred to fresh tubes, which were centrifuged again as above. The platelets were washed 3 times, avoiding contaminating erythrocytes at the bottom of the pellets. Pellets were consolidated at each step, and by the last wash with EDTA/KCl buffer, most of the erythrocytes were in 1 tube. The pellets were resuspended in buffer containing 10 mM Trizma 7.0 with 10 mM $CaCl_2$. Following centrifugation, the buffer was decanted and the pellets were resuspended in the $CaCl_2$ buffer, avoiding erythrocyte contamination by recovering less than 100% of the platelet pellets. The resuspended platelets were dispensed in 8-10 ml aliquots into Corex tubes and disrupted by three cycles of freezing (dry ice/ethanol) and thawing (24° C.). The tubes were centrifuged at $40,000 \times g$ for 20 minutes at 4° C. Supernatants were decanted and each pellet was resuspended in 5-7 ml 10 mM Trizma 7.0. All resuspended pellets were pooled and aliquots of about 1200 $\mu$l were dispensed into 1.5 ml microfuge tubes and frozen at $-70°$ C. Protein content was determined by a fluorescamine protein assay.

Assay Methods: Receptor Characterization—Each receptor preparation was evaluated to determine the number of receptor populations, the number of PAF receptor equivalents/mg protein and the dissociation constant ($K_D$) for PAF binding. This required 2-3 experiments in which the protein concentration was held constant and the $^3$H-PAF ligand concentration was varied from approximately 0.10-2.5 nM and the data was analyzed by Scatchard methodology. Total incubation volume was 250 μl for these procedures and incubations were conducted at 24° C. for 30 minutes. For further experimentation, total incubation volumes are 500 μl. Protein and ligand concentrations were adjusted to give 0.075 nM receptor equivalents in the presence of 0.75 nM $^3$H-PAF. Each receptor preparation was then used to determine the dose—response displacement relationship of unlabeled PAF and the PAF antagonist, triazolam. As long as the $K_D$ value and $IC_{50}$ values for PAF and triazolam were consistent with similar data collected from past receptor preparations used in the assay, the new receptor preparation was used for evaluating compounds.

Assay Methods: Routine Assay of Compounds—The compounds were weighed precisely and solubilized in quantities of DMSO such that a 5 μl aliquot in the incubate would deliver the desired compound concentration. Compounds tested for the first time in this assay were evaluated at a concentration of 50 μM in the incubation medium. All compounds were generally solubilized in DMSO for about 2 hours prior to assay. Triazolam was always included in each screening assay as a compound inhibition control. A standard concentration of 50 μM inhibited $^3$H-PAF binding by approximately 50%. Nonspecific binding control solution was made by drying to completion about 26.2 μl unlabeled PAF under a stream of argon. PAF was resolubilized in 1000 μl DMSO. When delivered in a 5 μl aliquot, the final concentration of 1 μM PAF in the incubate exceeded by 1000-fold the concentration of $^3$H-PAF.

All buffers containing proteins were made at room temperature on the day of assay. Assay buffer was prepared by adding 125 mg human albumin to 25 ml of stock buffer (10 mM Trizma 7.4 with 20 mM $CaCl_2$) Rinse buffer was made by adding 20 grams bovine serum albumin to 1000 ml stock buffer. About 80 ml of rinse buffer was decanted into a small pyrex dish and used to soak 65 Whatman GF/C 2.5 cm glass filters. The remaining rinse buffer was poured into a repipet and placed into an ice bath along with the filters.

Ligand for assay was prepared by adding about 10 μl of stock $^3$H-PAF (DuPont NEN, NET-668) to 14 ml of assay buffer. Since the amount of $^3$H-pAF in the final incubate was to be 0.75 nM, the actual amount of stock $^3$HPAF to be used had to be determined for each lot of material based upon its specific activity.

Membrane receptors for assay were prepared by thawing the appropriate number of tubes at room temperature and adding membranes to 10 mM Trizma 7.0 containing 10 mM $CaCl_2$. A total volume of 14 ml was made. The actual amount of membranes needed was determined by the requirement to have 0.075 nM PAF receptor equivalents per assay tube. All materials were kept in motion by rocking on a rocker plate.

First, 5 μl of compound or DMSO was added to each 12×75 mm polypropylene tube, followed by the addition of 95 μl assay buffer. Next, 200 μl $^3$H-PAF was added to each tube and 3 aliquots of $^3$H-PAF taken at different times during the dispensing were placed in scintillation vials. The reaction was initiated by the addition of 200 μl of membranes. All tubes were very briefly vortexed and placed in a 24° C. water bath for about 30 minutes. During this time, Whatman GF/C filters were placed on the filter racks of 5 Millipore vacuum manifolds. The incubations were terminated by first adding 4 ml ice-cold rinse buffer to each incubation tube and then decanting them over the filters under vacuum. Tubes and filters were rinsed twice more. Each filter was placed into a 20 ml scintillation vial to which 20 ml Aquasol (DuPont NEN, NDF 952) was added. All vials were given 2 hours in the dark for photo and chemiluminence to dissipate prior to liquid scintillation counting.

In summary, each incubation tube contained 500 μl total volume of incubate. This consisted of 5 μl drug with DMSO or only DMSO, 95 μl assay buffer, 200 μl $^3$H-PAF (0.75 nM final concentration) and 200 microliters membrane receptors (0.075 nM final concentration). 60 tubes per assay were run and each dose was performed in triplicate. Controls in every assay consisted of 2 diluent (DMSO) "0" controls (2 triplicate determinations placed at different positions within the 60 tube assay), 1 nonspecific binding control, and 1 triazolam drug control. The 16 remaining doses were used to test 16 different compounds at the screening dose of 50 μM, or to run dose-response determinations for a compound. In general, dose-response curves were composed of 4 compound doses designed to inhibit $^3$-PAF binding by 15-85%, with at least 1 dose on each side of the 50% point.

Routine Assay Calculations: Triplicate DPM determinations (corrected for background) within a single compound dose were averaged while all 6 determinations of total binding ("0" dose, DMSO only) were averaged. The amount for nonspecific binding (1 μM PAF) was subtracted from all the dose averages, giving an amount of specific binding in all cases. The percent displacement of $^3$H -PAF or inhibition of binding was calculated by the formula STBo-SBc/STBo×100, where STBo=specific binding of "0" dose controls and SBc=specific binding in the presence of compound. If a compound tested at the initial screening dose of 50 μM inhibited binding by 45% or more, the compound was considered active and was tested in a dose-response manner to determine an $IC_{50}$ value. Compounds inhibiting PAF binding by less than 45% at a 50 μM concentration were considered inactive and no further testing was done.

$IC_{50}$ values were determined on active compounds in subsequent tests. Three or more compound doses must inhibit $^3$H-PAF binding between 15-85%. Using a computer program, % displacement data was transformed (logit) and a least squares linear regression was performed on the data meeting the 15-85% requirement to determine $IC_{50}$ values from data points derived from the same assay.

| Compound | PAF induced platelet secretion (IC$_{50}$) | PAF induced platelet aggregation (IC$_{50}$) | Inhibition of $^3$H-PAF Binding to Human Platelet (IC$_{50}$) |
|---|---|---|---|
| N-cyclohexyl-5-[imadozo[4,5-c]pyridin-5-yl)methyl]-N-methyl-2-furancarboxamide | 50 μM | ca. 100 μM | 42% Inhib. (50 μM) |
| N-cyclohexyl-N-cyclopentyl-5-(5H-imidazol[4,5-c]pyridin-5-yl-methyl)-2-furancarboxamide | 2.8 μM | 10–100 μM | 37–62% Inhib. (50 μM) |
| N,N-dicyclopentyl-6-(5H-imidazol[4,5-c]pyridin-5-yl-methyl)-3-pyridinecarboxamide | 0.1–0.01 μM | 1.0–0.1 μM | 0.88 μM |

What we claim is:

1. A compound of the formula

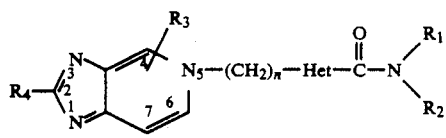

or a pharmaceutically acceptable acid addition salt thereof or isomers thereof: wherein R$_1$ and R$_2$ are each independently selected from hydrogen; straight or branched chain alkyl of 1 to 15 carbon atoms; cycloalkyl having 3 to 8 carbon atoms; cycloalkyl which can be substituted once or more by alkyl of 1 to 6 carbon atoms; phenyl; phenyl which can be substituted once or more by alkyl of 1 to 6 carbon atoms or halogen; straight or branched alkenyl having 3 to 15 carbon atoms with the proviso that the double bond of the alkenyl group cannot be adjacent to the nitrogen, Het is a heteroaromatic ring having 5 atoms wherein said atoms are selected from carbon, nitrogen, oxygen or sulfur and wherein any of the carbon atoms can be optionally substituted with a substituent independently selected from the group consisting of alkyl of 1 to 6 carbon atoms, alkoxy wherein the alkyl portion is 1 to 6 carbon atoms and halogen selected from bromo, fluoro, or chloro with the proviso that the carboxamide and imidazopyridine groups cannot be adjacent to each other and a nitrogen hetero atom of the heteroaryl ring is substituted by hydrogen or alkyl of 1 to 6 carbon atoms or HET is pyridine wherein any of the carbon atoms can be substituted with a substituent independently selected from the group consisting of alkyl of 1 to 6 carbon atoms; alkoxy wherein the alkyl portion is 1 to 6 carbon atoms and halogen selected from bromo, fluoro or chloro with the proviso that the carboxamide and imidazopyridine groups cannot be adjacent to each other, n is an integer from 1 to 5, R$_3$ is a group substituted at one or more of the 4, 6 or 7 positions of the pyridine ring said groups being independently selected from hydrogen, alkyl of 1 to 6 carbon atoms; halogen wherein the halogen is selected from bromo, fluoro, or chloro; or alkoxy wherein the alkyl portion is 1 to 6 carbon atoms.

R$_4$ is hydrogen or alkyl of 1 to 4 carbon atoms.

2. A compound according to claim 1 having the formula

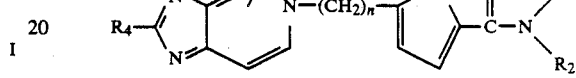

or a pharmaceutically acceptable acid addition salt thereof: wherein

R$_1$ and R$_2$ are each independently selected from hydrogen; straight or branched chain alkyl of 1 to 15 carbon atoms; cycloalkyl of 3 to 8 carbon atoms; cycloalkyl which can be substituted one or more by alkyl of 1 to 6 carbon atoms, R$_3$ is hydrogen or alkyl of 1 to 6 carbon atoms R$_4$ is hydrogen or alkyl of 1 to 4 carbon atoms n is an integer from 1 to 5, x is independently selected from the group consisting of O; S; N—R$_5$ wherein R$_5$ can be hydrogen or alkyl or 1 to 6 carbon atoms; or CH=N.

3. A compound according to claim, 1 having the formula

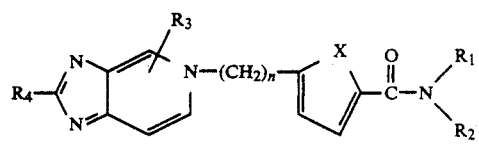

or a pharmaceutically acceptable acid addition salt thereof: wherein

R$_1$ and R$_2$ are each independently selected from hydrogen; straight or branched chain alkyl of 1 to 15 carbon atoms; cycloalkyl of 3 to 8 carbon atoms; cycloalkyl which can be substituted one or more by alkyl of 1 to 6 carbon atoms, R$_3$ is hydrogen or alkyl of 1 to 6 carbon atoms R$_4$ is hydrogen or alkyl of 1 to 4 carbon atoms n is an integer from 1 to 5 x is oxygen or CH=N.

4. A compound according to claim 3 which is N-cyclohexyl-N-cyclopentyl-5-[5H-imidazo[4,5-c]pyridin-5-yl-methyl]-2-furancarboxamide.

5. A compound according to claim 3 which is N,N,-dicyclopentyl-6-[5H-imidazo[4,5-c]pyridin-5-yl-methyl]-3-pyridinecarboxamide.

6. A compound according to claim 3 which is N-cyclohexyl-5-[5H-(imidazo[4,5-c]pyridin-5-yl)-methyl]-N-methyl-2-furancarboxamide.

7. A pharmaceutical composition useful for treating diseases or disorders mediated by platelet-activating factor comprising a compound according to claim 1, together with one or more non-toxic pharmaceutically acceptable carriers.

8. A pharmaceutical composition according to claim 7 wherein said compound is N-cyclohexyl-N-cyclopentyl-5-[5H-imidazo [4,5-c]pyridin-5-yl methyl]-2-furancarboxamide.

9. A pharmaceutical composition according to claim 7 wherein said compound is N,N,-dicyclopentyl-6-[5H-imidazo[4,5-c]pyridin-5 yl-methyl]-3-pyridinecarboxamide.

10. A pharmaceutical composition according to claim 7 wherein said compound is N-cyclohexyl-5-[5H-imidazo [4,5-c]pyridin-5-yl)methyl]-N-methyl-2-furancarboxamide.

11. A method for treating diseases or disorder, mediated by platelet-activating factor comprising administering a therapeutically effective dose of a compound of claim 1 to a mammal in need of such treatment.

12. A method according to claim 11 wherein said compound is N-cyclohexyl-N-cyclopentyl-5-[5H-imidazo[4,5-c]pyridin-5-yl-methyl]-2-furancarboxamide.

13. A method according to claim 1 wherein said compound is N,N,dicyclopentyl-6-[5H-imidazo[4,5-c]pyridin-5-yl-methyl]-3-pyridinecarboxamide.

14. A method according to claim 11 wherein said compound is N-cyclohexyl-5-[5H-imidazo[4,5-c]pyridin-5-yl) methyl]-N-methyl-2-furancarboxamide.

* * * * *

UNITED STATES PATENT AND TRADEMARK OFFICE
CERTIFICATE OF CORRECTION

PATENT NO. : 4,990,518

DATED : Feb. 5, 1991

INVENTOR(S) : Khanna, et. al.

Page 1 of 2

It is certified that error appears in the above-identified patent and that said Letters Patent is hereby corrected as shown below:

Column 8, line 65, reading "Dawson, et. al J Med" should read -- Dawson, et. al., J Med --.

Column 10, Scheme D, reading

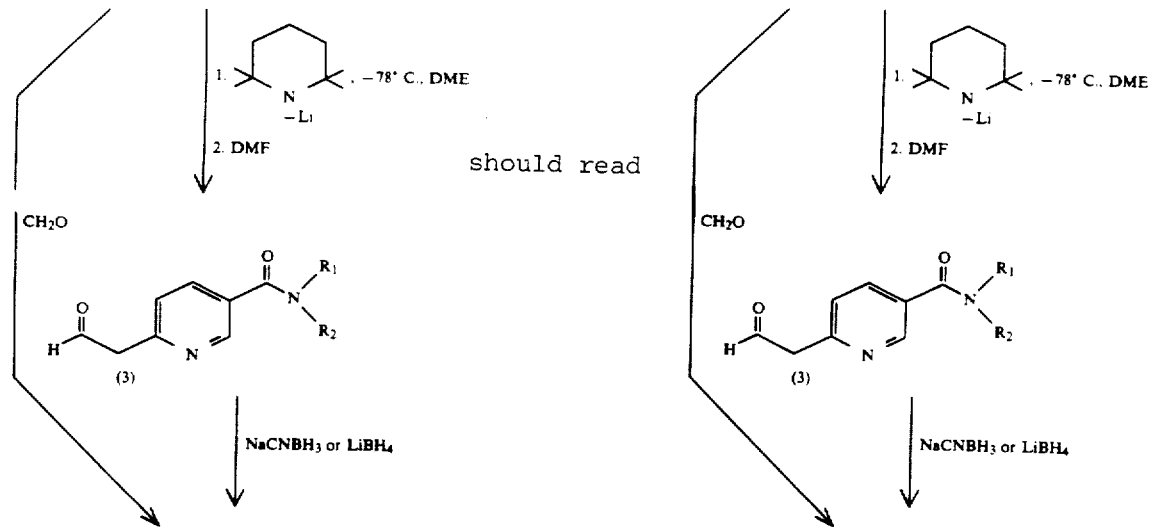

should read

UNITED STATES PATENT AND TRADEMARK OFFICE
CERTIFICATE OF CORRECTION

PATENT NO. : 4,990,518

DATED : Feb. 5, 1991

INVENTOR(S) : Khanna, et. al.

It is certified that error appears in the above-identified patent and that said Letters Patent is hereby corrected as shown below:

Column 11, line 37, reading "et al." should read -- et. al. --.

Column 12, line 39, reading "PPhd 3" should read -- $PPh_3$ --.

Column 22, line 32, reading "1H NMR" should read -- $^1H$ NMR --.

Column 24, line 59, reading "(chloromethyl) 2-furancarboxamide" should read -- (chloromethyl)-2-furancarboxamide --.

Column 34, line 9, reading "claim 1" should read -- claim 11 --.

Signed and Sealed this

Fifth Day of January, 1993

Attest:

DOUGLAS B. COMER

*Attesting Officer*   Acting Commissioner of Patents and Trademarks